(12) United States Patent
Hannay

(10) Patent No.: US 9,034,030 B2
(45) Date of Patent: May 19, 2015

(54) HELICAL ARM TIE DOWN

(75) Inventor: Gwynne Hannay, Queensland (AU)

(73) Assignee: Cook Medical Technologies LLC, Bloomington, IN (US)

( * ) Notice: Subject to any disclaimer, the term of this patent is extended or adjusted under 35 U.S.C. 154(b) by 653 days.

(21) Appl. No.: 12/075,531

(22) Filed: Mar. 12, 2008

(65) Prior Publication Data

US 2008/0228260 A1    Sep. 18, 2008

Related U.S. Application Data

(60) Provisional application No. 60/906,477, filed on Mar. 12, 2007.

(51) Int. Cl.
*A61F 2/06*   (2013.01)
*A61F 2/07*   (2013.01)
*A61F 2/95*   (2013.01)
*A61F 2/954*  (2013.01)
*A61F 2/82*   (2013.01)
*A61F 2/89*   (2013.01)

(52) U.S. Cl.
CPC ... *A61F 2/07* (2013.01); *A61F 2/95* (2013.01); *A61F 2/954* (2013.01); *A61F 2002/061* (2013.01); *A61F 2002/065* (2013.01); *A61F 2002/821* (2013.01); *A61F 2250/0098* (2013.01); *A61F 2/89* (2013.01); *A61F 2220/0075* (2013.01)

(58) Field of Classification Search
CPC ........................................................ A61F 2/07
USPC ........................................ 623/1.35, 1.23, 1.34
See application file for complete search history.

(56) References Cited

U.S. PATENT DOCUMENTS

| | | | |
|---|---|---|---|
| 6,471,722 | B1 | 10/2002 | Inoue |
| 7,105,020 | B2 | 9/2006 | Greenberg et al. |
| 2003/0120333 | A1 | 6/2003 | Ouriel et al. |
| 2004/0243221 | A1 | 12/2004 | Fawzi et al. |

FOREIGN PATENT DOCUMENTS

| | | |
|---|---|---|
| CA | 2518890 | 10/2004 |
| WO | WO 98/19630 | 5/1998 |
| WO | WO 99/22671 | 5/1999 |
| WO | WO 2006/113501 A1 | 10/2006 |
| WO | WO 2007/025101 A2 | 3/2007 |
| WO | PCT/US08/003319 | 7/2008 |

*Primary Examiner* — Jacqueline Woznicki
(74) *Attorney, Agent, or Firm* — Brinks Gilson & Lione

(57) ABSTRACT

An arrangement for temporarily retaining a side arm (36) of a stent graft (30) in a selected position during loading thereof onto a deployment device, the side arm extending from an ostium (38) in the tubular body (32) and substantially helically around and along the tubular body to an open end (40). A first tie down wire (48) is stitched through the tubular body and through the side arm and then through the biocompatible graft material of the tubular body at the open end of the side arm. The stent graft can then be loaded into a sheath of a deployment device for the stent graft. There can be a second tie down wire (50) stitched through the biocompatible graft material of the tubular body and through the side arm and then through the biocompatible graft material of the tubular body at the ostium end of the side arm. The first and/or second tie down wires can be withdrawn after the stent graft is loaded into the sheath or left in place until delivery.

8 Claims, 1 Drawing Sheet

HELICAL ARM TIE DOWN

CROSS-REFERENCE TO RELATED APPLICATIONS

This application claims priority of provisional application Ser. No. 60/906,477, filed Mar. 12, 2007.

TECHNICAL FIELD

This invention relates to a medical device and more particularly to an arrangement for assembly of a medical device onto an introduction device.

BACKGROUND OF THE INVENTION

This invention will be particularly discussed in relation to stent grafts for placement into the thoracoabdominal aorta for the treatment of aneurysms and more specifically in relation to juxtarenal placement. The invention, however, is not so restricted and may be applied to stent grafts for placement in any lumen of the human or animal body.

There has been devised a thoracoabdominal stent-graft with one or more side arms for the celiac, superior mesenteric and/or renal arteries. One particular form of stent graft includes a side arm which is a graft material tube which extends at least partially helically around the stent graft from a fenestration or ostium in the stent graft. Such a graft material tube can be formed from a corrugated graft material.

U.S. Pat. No. 7,105,020 entitled "Branched Vessel Endoluminal Device" describes various forms of helically extending side arm stent grafts and the teaching therein is incorporated herein in its entirety.

These helically extending side arm stent grafts may include radiopaque markers along the length of the helical branch to assist a physician with correct placement by radiographic techniques of the helically extending side arm stent graft into the aorta of a patient with the open end of the side arm directed towards a branch vessel of the aorta. The stent graft is constricted into an introduction device under a delivery sheath for introduction into a patient using endovascular techniques and during assembly onto the introduction device the side arm can be distorted out of its helical position. This can make the correct radiographic visualization of the position of the open end very difficult during the introduction procedure.

It is the object of this invention to provide an arrangement by which the side arm is constrained during assembly so that it remains in a desired position for introduction.

Although the invention will be generally discussed in relation to side arms for stent grafts which extend helically around a stent graft body the invention is not so restricted and may also be applied to other forms of side arm.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form the invention is said to reside in a stent graft comprising a tubular body of a biocompatible graft material and a side arm extending therefrom, the side arm extending from an ostium in the tubular body and at least partially along the tubular body to an open end of the side arm and a temporary tie down arrangement for the side arm at least adjacent to the open end, whereby to hold flat the open end of the side arm during loading of the stent graft into a deployment device to ensure the side arm is retained in its position with respect to the tubular body.

Preferably the temporary tie down arrangement comprises a tie down wire stitched into the graft material adjacent to the side arm and through the side arm to hold the side arm against the tubular body.

Preferably the side arm comprises a plurality of radiopaque markers therealong.

Preferably the side arm comprises a transversely corrugated graft material tube and the open end of the side arm extends at an angle of approximately 45° to the longitudinal direction of the stent graft.

Preferably the side arm comprises a resilient reinforcing ring at the open end thereof. The resilient reinforcing ring at the open end of the side arm can be permanently stitched to the tubular body. By this arrangement the resilient reinforcing ring at the open end of the side arm is held flat, with the open end against the tubular body, by the temporary tie down arrangement.

There can be further included a second temporary tie down arrangement for the side arm adjacent to hold flat the ostium end of the side arm during loading of the stent graft into a deployment device.

In one embodiment the temporary tie down arrangement is removed after the stent graft is loaded into a deployment device. Alternatively the temporary tie down arrangement is retained after the stent graft is loaded into a deployment device and the deployment device includes a release arrangement for the temporary tie down arrangement.

In one embodiment the side arm is a helical side arm which extends substantially helically around and along the tubular body of the stent graft.

In an alternative form the invention comprises a stent graft comprising a tubular body of a biocompatible graft material and a side arm extending therefrom, the side arm comprising a transversely corrugated graft material tube and a plurality of radiopaque markers therealong, the side arm extending from an ostium in the tubular body and substantially helically around and along the tubular body to an open end and the side arm comprising a resilient reinforcing ring permanently stitched to the tubular body at the open end thereof, a first temporary tie down arrangement comprising a tie down wire stitched into the graft material adjacent to the side arm and through the side arm to hold the side arm against the tubular body adjacent to the open end, and a second temporary tie down arrangement for the side arm at the ostium end thereof whereby to hold flat the open end of the side arm and the ostium end of the side arm during loading of the stent graft into a deployment device to ensure the side arm retains its position with respect to the tubular body.

In an alternative form the invention comprises a method of temporarily retaining a side arm of a stent graft in a selected position during loading thereof onto a deployment device, the stent graft comprising a tubular body of a biocompatible graft material and the side arm extending therefrom, the side arm comprising a plurality of radiopaque markers therealong, the side arm extending from an ostium in the tubular body and substantially helically around and along the tubular body to an open end;

The method including the steps of;

(a) stitching a first tie down wire through the biocompatible graft material of the tubular body and through the side arm and then through the biocompatible graft material of the tubular body at the open end of the side arm;

(b) stitching a second tie down wire through the biocompatible graft material of the tubular body and through the side arm and then through the biocompatible graft material of the tubular body at the ostium end of the side arm;

(c) loading the stent graft into a sheath of a deployment device for the stent graft; and (d) optionally removing the first and/or second tie down wires after the stent graft is loaded into the sheath.

BRIEF DESCRIPTION OF THE DRAWING

This then generally describes the invention but to assist with understanding reference will now be made to preferred embodiments with the assistance of the accompanying drawings in which.

DETAILED DESCRIPTION

Figure 1:
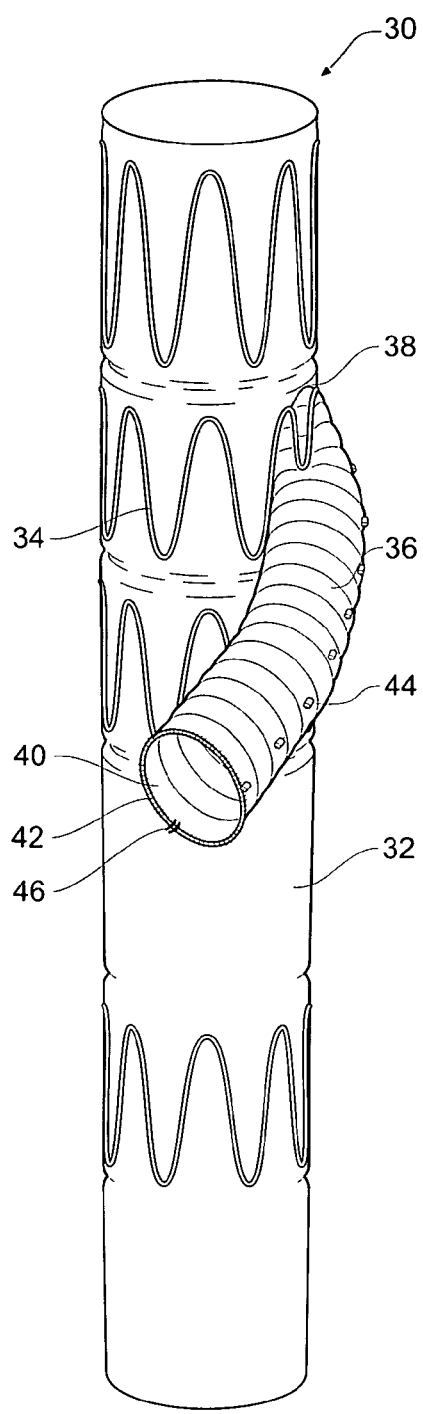
FIG. 1 shows a stent graft including a side arm according to one embodiment of the invention.
Figure 2:
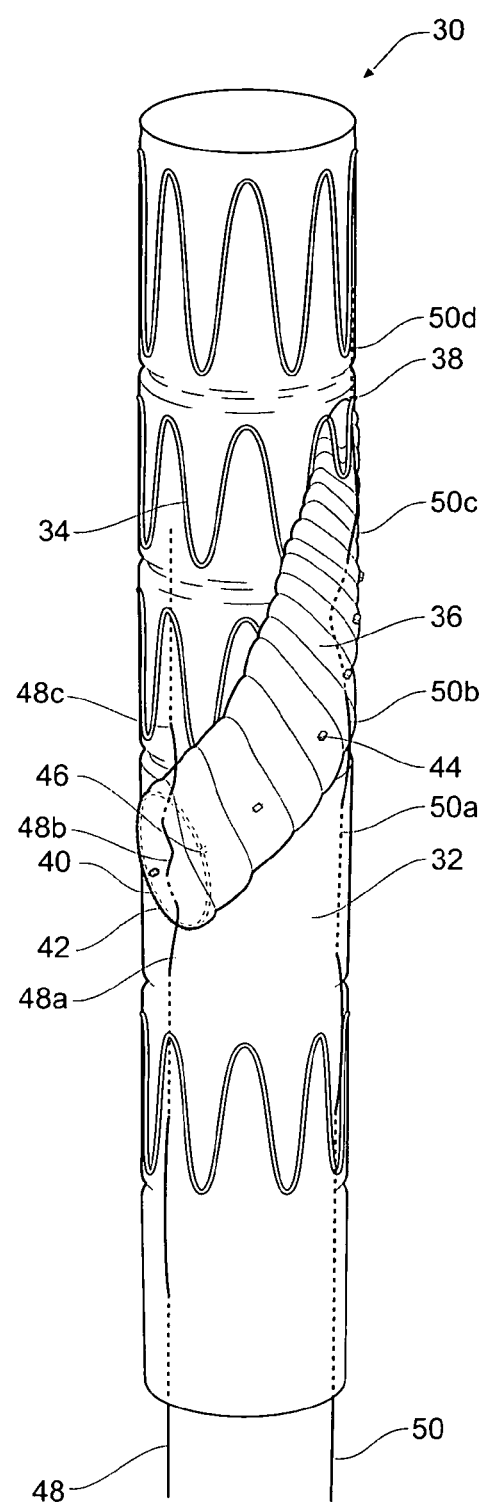
FIG. 2 shows the embodiment of FIG. 1 with two temporary tie down arrangements applied to it.

Looking at FIGS. 1 and 2 there is shown an embodiment of the invention.

In FIGS. 1 and 2 a stent graft 30 is formed from a tubular body 32 of a biocompatible graft material and has a plurality of zig-zag self expanding stents 34. A tubular side arm 36 extends from an ostium or fenestration 38 in the tubular body 32 in a part helical configuration along and around the tubular body 32 to an open end 40. The open end 20 is directed at an angle of approximately 45° to the longitudinal direction of the tubular body 32 and is reinforced by a resilient ring 42 stitched to the open end 40. The side arm 36 has a line of radiopaque markers 44 along its length. The tubular side arm 36 is formed from a corrugated biocompatible graft material tube and does not have any stents along its length. The resilient ring 42 is stitched to the tubular body 32 by stitching 46 to hold the open end in a desired position.

If the stent graft 30 was to be constricted and be forced into a sheath of a deployment device at least part of the side arm and the open end 40 of the side arm 36 could be dragged out of line with the length of the tubular body 32 which removes the helical form of the line of radiopaque markers 44 and makes it more difficult to visualize the position of the open end and place it in a desired position with respect to a side branch of a body vessel.

FIG. 2 shows the side arm 36 tied down by the use of a pair of tie down wires 48 and 50. A first tie down wire 48 is stitched through the graft material of the tubular body 32 at 48a, through the graft material of the side arm adjacent to the open end 40 at 48b and then through the graft material of the tubular body 32 on the other side of the side arm 36 at 48c. The tie down wire 48 holds the resilient ring 42, hinged about the stitching 46 with the open end 40 against the tubular body 32.

A second tie down wire 50 is stitched through the graft material of the tubular body 32 at 50a, through the graft material of the side arm towards the ostium end of the side arm at 50b, out of the side arm again at 50c and then through the graft material of the tubular body 32 on the other side of the ostium 38 of the side arm 36 at 50d.

By this arrangement the side arm is held in its desired position during constriction and loading onto a delivery sheath. This will assist in retaining the relative position of the helical line of radiopaque markers 24 with respect to the tubular body. As these can be visualized through the delivery sheath during an endovascular delivery operation the position of the open end 40 of the side arm can be determined and it will not significantly change when the delivery sheath is withdrawn.

After the stent graft has been placed into the delivery sheath in its constricted form (not shown) the tie down wires 48 and 50 can be withdrawn. Alternatively the tie down wires can be left in place and a suitable release mechanism provided on the delivery device to enable release at a selected time during the delivery procedure. It may be desirable to be able to rotate or move longitudinally the stent graft on the delivery device after withdrawal of the delivery sheath and before the side arm is released. This could prevent the side arm from fouling with the wall of the vessel during rotational and longitudinal movement.

Throughout this specification various indications have been given as to the scope of the invention but the invention is not limited to any one of these but may reside in two or more of these combined together. The examples are given only for illustration and not for limitation.

What is claimed is:

1. A stent graft comprising:
a tubular body of a biocompatible graft material, the tubular body having a circumference, a tubular body surface, an ostium in the tubular body surface, and a side arm extending from the ostium in the tubular body surface, and extending at least partially helically around and at least partially along the tubular body of the stent graft at least one-fourth the circumference of the tubular body to an open end of the side arm,
the stent graft further including a temporary tie down arrangement for the side arm, the temporary tie down arrangement comprising at least one elongate longitudinally extending wire extending proximally of the open end of the side arm to distally of the open end of the side arm, the at least one elongate wire passing through the tubular body surface at a location distal to the open end of the side arm, through the graft material of the side arm, and then through the tubular body surface at a location proximal to the open end of the side arm to hold the open end of the side arm against the tubular body surface by the tie down wire between distal and proximal locations, wherein the open end of the side arm is retained in its position with respect to the tubular body during loading of the stent graft into a deployment device, wherein the stent graft further includes a second temporary tie down arrangement for the side arm, the second temporary tie down arrangement comprising at least one elongate longitudinally extending wire extending proximally of the ostium end of the side arm to distally of the ostium of the side arm and holding flat the ostium end of the side arm during loading of the stent graft into a deployment device.

2. A stent graft as in claim 1 wherein the tie down wire is stitched into the graft material adjacent to the side arm and through the side arm holding the side arm against the tubular body surface.

3. A stent graft as in claim 1 wherein the side arm extends at an angle of approximately 45° to the longitudinal direction of the stent graft.

4. A stent graft as in claim 1 wherein the side arm comprises a plurality of radiopaque markers therealong.

5. A stent graft as in claim 1 wherein the side arm comprises a transversely corrugated graft material tube.

6. A stent graft comprising:
a tubular body of a biocompatible graft material, the tubular body having a circumference, a tubular body surface, an ostium in the tubular body surface, and a side arm extending from the ostium in the tubular body surface, and extending at least partially helically around and at least partially along the tubular body of the stent graft at least one-fourth the circumference of the tubular body to an open end of the side arm, the stent graft further including a temporary tie down arrangement for the side arm, the temporary tie down arrangement comprising at least one elongate longitudinally extending wire extending proximally of the open end of the side arm to distally of the open end of the side arm, the at least one elongate wire passing through the tubular body surface at a location distal to the open end of the side arm, through the graft material of the side arm, and then through the tubular body surface at a location proximal to the open end of the side arm to hold the open end of the side arm against the tubular body surface by the tie down wire between distal and proximal locations, wherein the open end of the side arm is retained in its position with respect to the tubular body during loading of the stent graft into a deployment device, wherein the side arm comprises a resilient reinforcing ring at the open end thereof, and wherein the resilient reinforcing ring at the open end of the side arm is held flat against the tubular body surface by the temporary tie down arrangement.

7. A stent graft as in claim 6 wherein the resilient reinforcing ring at the open end of the side arm is permanently stitched to the tubular body.

8. A stent graft comprising a tubular body of a biocompatible graft material, the tubular body having a circumference, a side wall, an ostium in the side wall, and a side arm extending from the ostium in the side wall of the tubular body and at least partially helically around and along the tubular body of the stent graft at least one-fourth the circumference of the tubular body to an open end, the side arm comprising a transversely corrugated graft material tube having a length, a plurality of radiopaque markers disposed along the length, and a resilient reinforcing ring at its open end that is permanently stitched to the tubular body, the stent graft further including a first temporary tie down arrangement comprising an elongate longitudinally extending tie down wire stitched through the graft material of the tubular body at, at least, two spaced-apart locations on the tubular body adjacent to the open end of the side arm, and through the side arm holding the open end of the side arm against the tubular body adjacent to the open end between the two spaced apart locations, wherein one spaced apart location is proximal to the open and of the side arm and the other spaced apart location is distal to the open end of the side arm, and a second elongate longitudinally extending temporary tie down arrangement for the side arm at the ostium end of the side arm holding flat the open end of the side arm and the ostium end of the side arm during loading of the stent graft into a deployment device to ensure the side arm retains its position with respect to the tubular body.

* * * * *